US00RE34579E

United States Patent [19]

Buyske, deceased et al.

[11] E Patent Number: Re. 34,579

[45] Reissued Date of Patent: Apr. 5, 1994

[54] METHOD OF TREATING DEPRESSION

[75] Inventors: Donald A. Buyske, deceased, late of Lake Worth, Fla.; by Susan G. Buyske, administratrix, New York, N.Y.

[73] Assignee: Somerset Pharmaceuticals, Inc., Tampa, Fla.

[21] Appl. No.: 750,292

[22] Filed: Aug. 27, 1991

Related U.S. Patent Documents

Reissue of:

[64] Patent No.: 4,868,218
Issued: Sep. 19, 1989
Appl. No.: 339,712
Filed: Apr. 18, 1989

U.S. Applications:

[62] Division of Ser. No. 86,795, Aug. 18, 1987, Pat. No. 4,861,800.

[51] Int. Cl.[5] ..... A61K 31/135

[52] U.S. Cl. ..... 514/646; 514/946; 514/947; 514/969

[58] Field of Search ..... 514/646, 946, 947, 969

[56] References Cited

U.S. PATENT DOCUMENTS

| | | | |
|---|---|---|---|
| 2,997,422 | 8/1961 | Tedeschi . | |
| 4,230,105 | 10/1980 | Harwood . | |
| 4,284,444 | 8/1981 | Bernstein et al. . | |
| 4,409,243 | 10/1983 | Lieb . | |
| 4,568,343 | 2/1986 | Leeper et al. . | |
| 4,812,481 | 3/1989 | Reischig et al. . | |
| 4,885,154 | 12/1989 | Cormier et al. . | |
| 4,925,878 | 5/1990 | Bodo et al. . | |
| 5,030,629 | 7/1991 | Rajadhyaksha | 514/946 |
| 5,045,317 | 9/1991 | Chess et al. | 514/946 |
| 5,049,387 | 9/1991 | Amkraut . | |

FOREIGN PATENT DOCUMENTS

| | | |
|---|---|---|
| 0139127 | 8/1984 | European Pat. Off. . |
| 2.635M | 4/1963 | France . |
| 2163347A | 2/1986 | United Kingdom . |

OTHER PUBLICATIONS

Chem. Abst. 97-138,580q (1982).
Chem. Abst. 101—122860e (1984).
Martindale, The Extra Pharmacopoeia, Twenty-Eighth Edition, pp. 1752-753, Pharmaceutical Press, 1982.
Gardner, Targeting the Central Nervous System: New Drug Delivery Technologies for Psychotropic Agents, vol. 21, No. 3, 1985, pp. 657-662.
Koller et al., PHNO, A Novel Dopamine Agonist, in Animal Models of Parkinsonism, Movement Disorders, vol. 2, No. 3, pp. 193-199, 1987.

*Primary Examiner*—S. J. Friedman
*Attorney, Agent, or Firm*—Mathews, Woodbridge & Collins

[57] ABSTRACT

The monamine oxidase inhibitor drug L-deprenyl (phenylisopropyl methyl propynyl amine) is safely and conveniently used for the treatment of mental depression in a formulation applied to the skin of the patient. In this way the danger of side reaction due to the consumption of foods containing tyramine (the cheese effect) is minimized. Unlike other monamine oxidase drugs, such as Parnate, L-deprenyl does not cause skin irritation when used in this way.

12 Claims, No Drawings

METHOD OF TREATING DEPRESSION

Matter enclosed in heavy brackets [ ] appears in the original patent but forms no part of this reissue specification; matter printed in italics indicates the additions made by reissue.

CROSS REFERENCE TO RELATED APPLICATION

[This application is a division of my copending application Ser. No. 07/086,795, filed 18 Aug. 1987.] *This application is a reissue of Ser. No. 339,712 filed Apr. 18, 1989, now U.S. Pat. No. 4,868,218, which is a division of Ser. No. 086,795, filed Aug. 18, 1987, now U.S. Pat. No. 4,861,800.*

FIELD OF THE INVENTION

My present invention relates to the therapeutic administration of the drug L-deprenyl a method of treating human subjects suffering from depression and, more particularly, to (levo phenyl isopropyl methyl propynyl amine) for this purpose. For brevity, L-deprenyl will often be denoted as LDY.

BACKGROUND OF THE INVENTION

Two general classes of organic pharmaceuticals useful in the treatment of the mental disease depression in humans have been recognized: (1) tricyclic antidepressants, as exemplified by amitriptyline and protriptylene, and (2) monoamine oxidase inhibitors (MAOI), as exemplified by the commercially available drugs Nardil, Parnate, and L-deprenyl.

Both types of drugs are generally regarded as effective, but both have undesirable side effects. For tricyclic drugs, recognized side effects include dry mouth, orthostatic hypotension, and impotence, and these effects are frequent. The most significant side effect of the MAOI drugs is a rare but serious one: sudden and dangerous life-threatening elevation of blood pressure when the patent taking such drugs also consumes foods high in the naturally occurring substance tyramine. Cheese is the most common food containing large amounts of tyramine, so that this side effect is often known colloquially in the medical profession as the "cheese effect".

Because the cheese effect can cause very serious medical problems, including death in severe cases, MAOI drugs are little used, even though they are generally free from the other more common side effects of the tricyclic drugs and are believed to have at least equal effectiveness in the treatment of most types of depression.

Tyramine is known to be capable of causing severe hypertension when presented in the blood, but it is normally converted in the gastrointestinal tract by the action of a monoamine oxidase enzyme naturally present there, to other substances incapable of causing dangerous hypertension. When a patient is taking an MAOI orally, however, deactiviation of the tyramine by gastrointestinal enzymes is at least partially repressed, and serious clinical symptons may result.

Recent research has recognized a distinction among the MAOI drugs themselves, connected with recognition of the existence of two isozymes of monoamine oxidase itself, denoted simply as the A and B isozymes. Nardil and Parnate are recognized as primarily inhibitors of the action of monoamine oxidase A, while deprenyl first inhibits the action of monoamine oxidase B and significantly inhibits the action of monoamine oxidase A only at larger doses. The tyramine deactivating monoamine oxidase enzyme is primarily type A, so that it would appear that administration of L-deprenyl should not induce the cheese effect. The cheese effect, however, is potentially so serious that, the use of L-deprenyl in an oral dosage is nevertheless counterindicated simply because it does appear to have some MAO-A inhibiting activity. On the other hand, the monoamine oxidases in the brain are primarily of the B type, so that LDY is very effective in inhibiting their action.

There are three general modes of administration which have been used for the antidepressants under consideration, which must reach the blood stream in the course of exerting their therapeutic effects: oral, intravascular, and transdermal. Because of the danger of infection and the need for trained personnel for administration, intravascular administration is disfavored when one of the other two means is effective. Drugs for treating depression have traditionally been administered orally, but transdermal administration of some of the tricyclic antidepressant drugs, and by implication, any suitable drug, has also been taught by U.S. Pat. No. 4,230,105 of Oct. 28, 1980 to Harwood. Transdermal administration of drugs in general has been taught by earlier patents, including some cited in the Harwood reference.

One highly restrictive limitation on the transdermal administration of drugs is the possibility of skin irritation or allergic reactions induced by such administration. This is particularly important when considering treatment of depression since MAO inhibitors are required to be used at higher dose levels.

In Whatever dosage form it may be administered, an antidepressant drug must be constantly present in the body for up to six months if the patient is to derive maximum benefit and not revert to a depressed state.

If transdermal administration of an antidepressant is to be used, this means very prolonged and constant or near-constant contact between the patient's skin and the pharmaceutical including the drug. It is well known that long-term exposure of skin to a chemical substance even at low dosages often will result either in a local skin inflammation at the side of contact or a more general immunologically based allergic reaction that can have a serious adverse effect on the entire body. When either of these events occur, the affected patient should immediately discontinue contact with the offending agent. Since MAO inhibitors generally were found heretofore to be skin irritants, clearly their use for antidepression treatment by transdermal techniques was not indicated.

SUMMARY OF THE INVENTION

I have found, most surprisingly, that LDY, applied to a suitable form and amount to human skin, is readily absorbed through the skin into the bloodstream to achieve and maintain a level in the blood, including the blood in the brain, which is effective in the treatment of depression.

Furthermore, while other MAO inhibitors are highly irritating to the skin, surprisingly, it has been found that LDY causes little or no skin irritation, by contrast with Parnate, for example, which is strongly irritating to the skin. Thus, transdermal administration of LDY provides a surprisingly nonirritating and effective method for treating depression.

SPECIFIC DESCRIPTION

For a normal human adult, about 30 mg of deprenyl per day is normally an effective dose for a relief of depression. This may be adjusted to blood volume of a particular patient by calculations well-known in the medical arts. The drug is preferably used either as free base or as its hydrochloride. For convenience in dispensing, the drug usually is mixed with other pharmaceutically inert materials. These inert materials, also called excipients, can be formulated by methods known in the prior art so as to promote either rapid absorption of most of the drug content applied to the skin, or a slower absorption over a longer time.

In treating most patients for depression, it is preferable to use a formulation, which will result in an approximately constant level of the antidepressant drug in the blood supply to the brain. After a possibly different initial treatment, such a constant level of drug in the blood will normally result from a constant rate of absorption from the applied drug mixture through the patient's skin into the bloodstream.

A mixture of LDY with appropriate excipients may effectively be utilized in a skin patch structure, of any of several types known to the art which will maintain the drug mixture in effective contact with the skin, protect against deteriorations in the drug which might be caused by such common causes as air oxidation, moisture absorption or loss, etc., and stay in position under normal conditions of patient mobility and bathing. The prepared patch structure, including a mixture of LDY in contact with the skin, may be applied to the skin of a patient in any of the locations on the body conventionally used for application of transdermal medications.

In order to promote consistent therapy with poorly motivated, easily distracted, or otherwise less-than-ideally-attentive patients—types particularly likely to be countered in the treatment of depression—it is advantageous for the supply of LDY in a single therapeutic structure to last for at least one full day. Structures lasting several days, or even weeks, are still more preferable as they require less patient attention.

The scope and nature of the invention may be further appreciated from the following non-limiting examples. In all the examples, all specifications of parts and percentages in formulations refer to parts and percentages by weight, and the dosage specified may be adjusted to the exact needs of an individual patient and accurately dispensed by conventional techniques known in the medical arts.

EXAMPLE 1

A suitable mixture for treatment according to this invention, consists of 3 parts of L-deprenyl mixed with 97 parts of an ointment base. The composition of the ointment base is as follows:

| | |
|---|---|
| Polyethylene glycol 6000 distearate | 5–15% |
| Polyethylene glycol 1540 | 15–25% |
| Butylated hydroxytoluene preservative | 0.1–.1–0–5% |
| Polyethylene glycol 300 | Balance |

An amount of 0.5 to 2.0 grams of this medicated ointment is applied to the forearm of a patient suffering from depression and rubbed into the skin to provide a therapeutically effective amount of L-deprenyl for at least one day.

EXAMPLE 2

This is the same as Example 1, and is used in the same way, except that the base is a cream rather than an ointment. The composition of the cream base is:

| | |
|---|---|
| Glyceryl monostearate NF VII | 10–20% |
| Cetyl alcohol | 5–10% |
| Cetyl ester wax | 5–10% |
| Polysorbate 60 | 5–10% |
| Propylene glycol | 5–10% |
| Dimethicone 350 | 0.5–3% |
| Paraban preservative | 0.2% |
| Water | Balance |

EXAMPLE 3

This is an example of a transdermal patch incorporating LDY. Five to fifty milligrams of this drug is dissolved in a mixture of mineral oil and poly (isobutylene) to provide a liquid-center reservoir of active drug. This reservoir is enclosed in a sealed, flat disc-shaped pouch, one to six centimeters in diameter. The top of the pouch consists of a thin aluminized polyester film that is impermeable to the pouch contents. The bottom of the pouch that will be in contact with the skin in use consists of thin polypropylene membrane that is slowly porous to LDY, allowing the drug to continuously come into contact with the skin, so long as the bottom of the pouch is in contact with the skin. This bottom of the pouch also includes a thin coat of a hypoallergenic silicone adhesive disposed on the bottom in such a way as to hold the patch firmly to the skin without unduly impeding the permeation of the drug through the membrane. As manufactured, a protective strip of siliconized polyester film covers the polypropylene membrane. This siliconized film is impermeable to the liquid mixture and thus protects the pouch's therapeutic contents during storage. The protective film is removed by the patent prior to the attachment of the patch to the skin.

EXAMPLE 4

The general construction of the therapeutic device for this example is the same as for Example 3, except that (1) the LDY is mixed with 50 mg of lactose, 50 mg of finely divided silicon dioxide, and 0.1 to 0.4 milliliters of medical-grade silicone fluid to form the reservoir of active drug and (2) the bottom of the patch consists of a thin ethylene-vinyl acetate copolymer membrane. The product is used in the same manner as in Example 3.

EXAMPLE 5

For this example, a solution or finely divided emulsion of L-deprenyl is prepared in a dispersion in water, or alternatively in a co-dispersion with a binder such as polyvinyl chloride. Geon 576, a product of B. F. Goodrich, is a suitable dispersion of binder into which LDY can be do-dispersed. The emulsion is dried onto a thin solid film of polyvinyl chloride or polypropylene plastic, which is slowly permeable to LDY to give a flat disc 1 to 6 centimeters in diameter. The top surface of the patch, the provision of a protective cover on the bottom for storage, and the optional use of a hypoallergenic adhesive on the outside of the bottom of the patch are the same as in the previous examples. The type of skin patch used for this example is described in more detail in U.S. Pat. No. 4,284,444.

It is well known in the medical arts that a patch maintained in tight contact with the skin will provide an occlusive cover. This will induce changes in the cellular architecture of the skin, including an increase in its water content. These changes allow LDY to migrate from the dried reservoir in the patch through the skin into the systemic blood circulation.

I claim:

1. A method of treating depression in a human patient which comprises maintaining in contact with the skin of said patient a quantity of L-deprenyl or a salt thereof in a form permitting migration of said L-deprenyl or salt thereof through the skin of said patient into the bloodstream of the patient to a sufficient extent to produce a therapeutically effective amount of L-deprenyl within the blood supply to the brain of said patient without causing skin irritation to the patient or inducing a cheese effect in the patient.

2. The method defined in claim 1 wherein said L-deprenyl or salt thereof is mixed with an excipient before being applied to the skin of said patient.

3. The method defined in claim 2 wherein said excipient causes the L-deprenyl content of the mixture to migrate into the bloodstream of the patient at a controlled rate, whereby at least said therapeutically effective amount of L-deprenyl is maintained in the blood supply to the brain of said patient continuously throughout a time interval.

4. The method defined in claim 3 wherein said mixture containing L-deprenyl is contained within a patch structure for convenient affixation to a part of the body of said patient in such a manner as to maintain contact between the skin of said patient and said mixture containing L-deprenyl during said time interval.

5. The method defined in claim 4 wherein said time interval is at least one day.

6. A method, according to claim 5, wherein said controlled rate is between 5 and 50 mg of L-deprenyl per day.

*7. A topical composition for the transdermal administration of L-deprenyl or a salt thereof, comprising a quantity of L-deprenyl or a salt thereof as a sole therapeutically active agent effective upon transdermal migration into the bloodstream to inhibit monoamine oxidase B, in combination with at least one pharmaceutical carrier operable to permit transdermal absorption of L-deprenyl or a salt thereof.*

*8. The topical composition according to claim 7 wherein the quantity of L-deprenyl or a salt thereof is sufficient to provide from about 5 to about 50 mg of L-deprenyl per day to a patient.*

*9. The topical composition according to claim 7 wherein the carrier is an ointment base.*

*10. The topical composition according to claim 7 wherein the carrier is a cream base.*

*11. The topical composition according to claim 7 wherein the composition is incorporated into a transdermal patch structure.*

*12. The topical composition according to claim 11 wherein the transdermal patch structure comprises a sealed pouch having a top layer impervious to the composition and a bottom membrane for dermal contact through which said L-deprenyl or a salt thereof is slowly porous.*

* * * * *